United States Patent [19]

MersKelly et al.

[11] Patent Number: 5,681,742
[45] Date of Patent: Oct. 28, 1997

[54] BIOLOGICAL SPECIMEN CONTAINMENT AND INCUBATION DEVICE

[75] Inventors: William C. MersKelly, Xenia, Ohio; David Y. Phelps, Louisville, Ky.

[73] Assignee: Louisville Laboratories, Inc., Louisville, Ky.

[21] Appl. No.: 534,051

[22] Filed: Sep. 26, 1995

[51] Int. Cl.$^6$ .................... C12M 1/24; C12Q 1/24
[52] U.S. Cl. ................ 435/288.1; 435/288.2; 435/304.1; 435/309.2; 435/30; 422/102; 436/180; 215/307; 215/311; 222/490; 222/499; 222/525; 141/319; 141/320
[58] Field of Search .................. 435/30, 288.1, 435/304.1, 307.1, 309.1, 309.2, 304.2; 422/100, 102; 436/180; 215/247, 248, 307, 308, 310, 311, 355, 363; 220/360, 361, 363, 367.1; 222/490, 498, 499, 511, 513, 514, 518, 522, 523, 525, 562, 563; 141/319, 320

[56] References Cited

U.S. PATENT DOCUMENTS

| 515,626 | 2/1894 | Schafer | 215/307 |
|---|---|---|---|
| 558,848 | 4/1896 | Schafer | 215/307 |
| 820,987 | 5/1906 | Perotti | 215/311 |
| 2,309,895 | 2/1943 | Griffith | 222/490 |
| 2,638,613 | 5/1953 | Gunther . | |
| 2,665,037 | 1/1954 | Zublin | 222/525 |
| 2,797,837 | 7/1957 | Roberts . | |
| 3,143,255 | 8/1964 | Leeds | 222/563 |
| 3,232,499 | 2/1966 | Esposito | 222/499 |
| 3,977,400 | 8/1976 | Moorehead | 215/311 |
| 4,355,111 | 10/1982 | Shimizu et al. | 215/307 |
| 4,515,752 | 5/1985 | Miramanda | 215/307 |
| 5,135,865 | 8/1992 | Ranoux | 435/240.2 |
| 5,422,240 | 6/1995 | Lytle et al. | 435/287.1 |

FOREIGN PATENT DOCUMENTS 650458  12/1962  Italy .................. 215/307

Primary Examiner—William H. Beisner
Attorney, Agent, or Firm—Don Halgren

[57] ABSTRACT

The present invention relates to a biological specimen and incubation container having a cylindrically shaped housing having a closed first end and an open second end. A plug, having a longitudinal bore therethrough, is anchored into a first position at the open end of the container. The container may then be supplied, via a pipette, through that bore in the plug. When the container is filled, the plug may be pushed further into the container, where it is squeezed by intermating tapered surfaces, to close the bore therein. An arrangement of annular lips and grooves in the container and the plug, anchors the plug to the container and ultimately seals and secures them together.

12 Claims, 2 Drawing Sheets

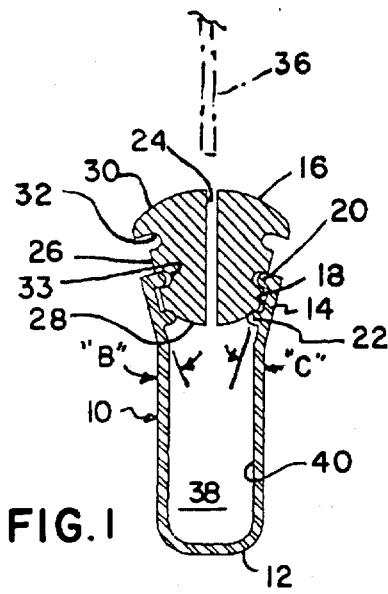
FIG.1
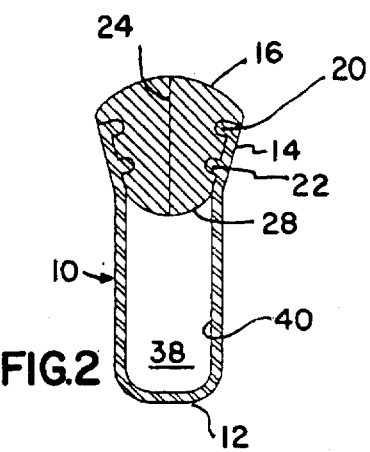
FIG.2
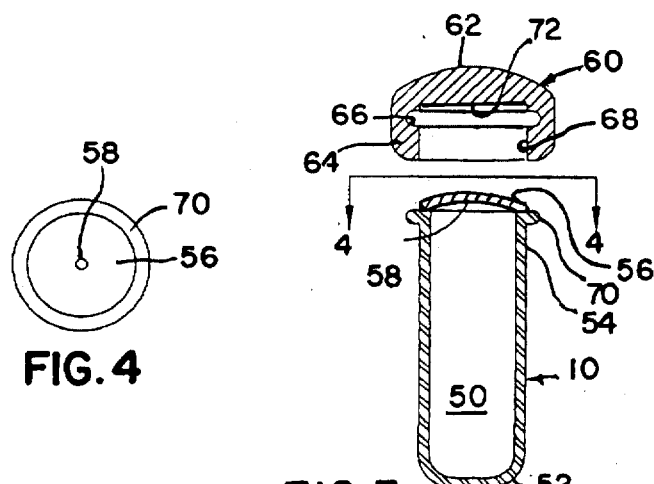
FIG.3
FIG.4
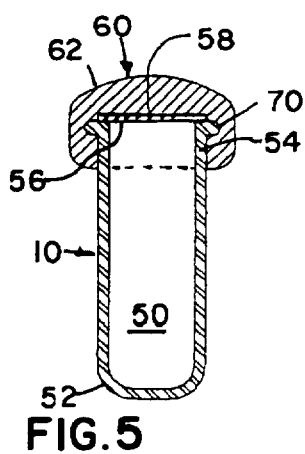
FIG.5

BIOLOGICAL SPECIMEN CONTAINMENT AND INCUBATION DEVICE

BACKGROUND OF THE INVENTION

1. Field of the invention

This invention relates to biological specimen containment devices, and more particularly to a chamber useful for in vitro fertilization cultures.

2. Prior Art

Containment devices for biological specimens often are restricted in their design function. The devices often must not permit light to strike the medium within the container. The device must not have sharp edges which would bind or unintentionally agitate the medium within the container. The device must also often permit the medium to be maintained at a desired precise temperature, and the device must often minimize the exposure of the medium to the atmosphere.

One such containment device is shown in U.S. Pat. No. 4,598,045 to Masover et al. issued on 1 Jul. 1986. This patent discloses a container shaped like a cylinder, having a screw on cap. The container however, is designed to permit microscopic examination of the medium without opening of the container.

A further biological specimen containment device is shown in U.S. Pat. No. 4,761,379 to Williams et al. This device however, utilizes a wide-natured opening, which could expose many biological specimens to the atmosphere for too long a period of time, and as such, would not be useful for procedures involving specimens for example, in vitro fertilization processes because of potential atmospheric contamination.

A further biological container is described in U.S. Pat. No. 5,135,865 to Ranoux, wherein a thin walled tube having a rounded lower end and a screw-on cap on its upper end, for containment and fertilization of human ovocytes with minimal $CO_2$ exposure to the medium.

It is an object of the present invention to provide a biological specimen container which overcomes the disadvantages of the prior art.

BRIEF SUMMARY OF THE INVENTION

The present invention relates to a biological specimen containment tube specifically for intra-vaginal placement of fertilized ovocytes.

The containment tube is generally of cylindrical configuration having a hemispherical shape thereon. The container has a second open end which is atmospherically sealable by a resilient plug longitudinally movably disposed therein. The second end of the containment tube has a slight outward directed flare with respect to the axis of the containment tube. The second end of the tube has an inner wall which tapers to provide a decreasing inside diameter of the container in the direction away from the second end of the tube. A second radially inwardly directed annular lip is disposed on the inner wall surface, spaced apart from the first annular lip, the second annular lip being arranged slightly closer toward the middle of the containment tube.

The resilient plug disposed in the second open end of the containment tube is initially at a first position when only on lip is in one groove. The plug has a narrow diameter, longitudinally directed central bore therethrough. The plug also has a slightly tapered outer annular surface, which increases in diameter from an inside edge to its outer cap.

The first inwardly directed annular lip engages with a first annular groove in the outer annular surface of the plug, when the plug is arranged in its first position, which position permits the central bore therethrough, to remain opened for the insertion of a pipette into the chamber defined by the inner wall of the containment tube.

The plug may be pressed inwardly into the containment tube, towards the first end, and further within the tapering walls of the second end of the tube, where the walls of the tube and the second annular lip tightly engage the first and a second annular wall of the plug. The resilient plug is thereby squeezed radially inwardly effectively blocking the longitudinally bore extending therethrough, thus sealing whatever medium/culture has been inserted into the chamber through that bore.

A further embodiment of the containment tube includes a second end having an ovoid resilient-walled cap sealed thereon. The resilient-walled cap has a central opening through which a pipette may be inserted for depositing of a specimen within the containment tube.

A cover is engagably sealable over the resilient cap. The cover has a hemispherical solid dome with an annular lip which extends off the edge of the hemispherical dome. And annular groove is arranged on the inner wall of the annular lip to engage an annular lip directed radially outwardly at the open end of the containment unit. A planar surface is arranged across the inside of the hemispherical dome.

Placement of the cover over the second end of the containment tube causes the planar surface to frictionally engage the ovoid resilient-walled cap and displace it angularly inwardly towards the first end of the containment tube. The angular displacement brings the central opening to a close, and the annular lip of the cover sealing engages the outer side walls of the second end of the containment tube, thus absolutely minimizing any exposure time of any medium/culture to atmospheric gases or $CO_2$, providing a superior environment for cultivation and incubation of any ovocytes within the chamber.

The invention thus comprises a biological specimen container device comprising an elongated specimen container unit having a rounded closed first end an open second end, a cylindrically shaped containment wall disposed between the closed first end and the open second end, and a self-sealing cap arranged anchored to the second end of the container in a first position and sealingly secured to the second end of the container in a second position thereat, the cap permitting deposit of material within the container while the cap is anchored in its first position. The self-sealing cap and the second end of containment unit have a multiple lip and groove engagement arrangement therebetween, to permit anchoring and subsequent sealing of the container unit when the cap is moved from its first position to its second position. The self-sealing cap has a squeezingly closable bore disposed longitudinally therethrough. The cap comprises a plug having a tapered outer wall, the tapered outer wall having a first and second spaced apart annular grooves therearound.

The open second end of the containment unit has a first and a second radially inwardly directed annular lip, the first and second annular lips being spaced apart a distance which corresponds to the distance between the spaced apart annular grooves of the plug. The plug has an inner end which is spaced from the second annular groove a shorter distance than the distance of the spaced apart annular grooves on the plug. The tapered outer wall tapers at an angle of about 10 to 20 degrees with respect to the longitudinal axis of the containment unit. The plug has walls which taper at an angle of about 10 to 25 degrees with respect to the longitudinal axis of the containment unit.

The invention includes a method of utilizing a biological specimen container, comprising the steps of arranging a cylindrically shaped containment unit, having a rounded closed first end and an open second end, inserting an anchorable flexibly sealable plug in a first position in the open second end of the containment unit the plug having a patent bore extending longitudinally therethrough, placing a pipette with biological specimens therein, through the bore in the plug, and into the containment unit, releasing the biological specimens in the containment unit, withdrawing the pipette from the patent bore of the plug, and pushing the plug from a first anchored position in the open end of the containment unit, to a second sealing position in the containment unit, where the patent bore has been squeezed closed to effectively seal the biological specimen within the biological specimen container. The method includes arranging a taper in the walls of the open end of the container unit, arranging a pair of spaced apart annular lips radially inwardly on the open end of the container unit, and arranging a pair of spaced apart annular grooves on the plug which are engagable with the annular lips on the container unit to ensure a sealed relationship therebetween.

The invention further comprises a biological specimen container device having an elongated specimen container unit with a rounded first closed end and an open second end, a cylindrically shaped containment wall disposed between the first end and the open second end, a flexible cap anchored to the open second end, the cap having an opening therein for receipt of a specimen delivery tube therethrough, the cap being distortable when moved from a first orientation to a second orientation, so that the opening therethrough is changed from a patent opening to a squeezed closed configuration, the cap thus permitting deposit of material within the container unit while the cap is in its first position. The flexible cap is of ovoid shape, and has a cover which mates thereover, so as to bias the cap into a second orientation effectively closing the opening in the cap and also proving a further seal to the container unit. The cover has an annular lip thereon, to sealingly engage the cylindrically shaped wall of the containment unit. The cover has an annular groove on an inner wall surface of the annular lip, the annular groove being arranged to mate with a radially outwardly directed annular lip on the cylindrically shaped wall on the second end of the containment unit, to further seal any specimen in the containment unit.

A further embodiment includes a pair of containment tubes which may be joined by a single double-ended plug. Each containment tube may be similar to the tube described hereinabove. The double ended plug 84 is essentially a mating of two plugs joined each at their respective outer curved cap and having a common longitudinally aligned bore therethrough.

The double ended plug has a pair of annular grooves at each of its respective side wall lips portions. The second groove mates first with a first lip on each tube and subsequently, when each tube is filled with a medium, both pairs of grooves will mate with their respective lips.

There may be a desire to transfer the contents of one tube into another tube, without exposing any medium such as an embryo to the atmosphere, because such exposure would rapidly change the pH of any growth media and likely contaminate or kill any embryo therewithin. One tube would be filled and a double ended plug then be inserted into its open end to seal it, locking both grooves with both lips. The second tube may then be filled with a medium and the other end of the now inverted double ended plug being pressed into the open end of the second tube. Transfer of an embryo from one tube into the other tube can be effected by backing out each end of the plug to its outermost groove, thus "unsqueezing" the bore, permitting embryo/medium to be exchanged from one tube to the other tube without exposure to the atmosphere.

The invention further contemplates a pH indicator such as a litmus paper strip attached at or near the rounded inner end of the plug. Each tube, in any embodiment described herein, may have a exposed markable surface to permit marking thereon, as by etching or the like for identification purposes.

The invention thus further comprises a biological specimen container having a self-sealing cap with a pair of tapered ends, each end having an arrangement of annular grooves thereon, for sealing a first container and a second container, in longitudinal alignment, each of the containers having corresponding annular lips thereon to mate with the grooves of the cap. The self-sealing cap has a mid-portion of wider diameter than the ends thereof, and a longitudinal bore extending therethrough, to permit fluid communication between the first and second containers disposed on respective ends of the cap.

The fluid content of one container may be transferred to the second container by loosening each end of the cap in its respective container, to permit the bore therein to become "unsqueezed", and thereby patent, to permit such transfer without atmospheric contamination. The biological specimen container cap may have a pH indicator strip such as litmus paper attached thereon to indicate whether any pH level has been reached.

BRIEF DESCRIPTION OF THE DRAWINGS

The objects and advantages of the present invention will become more apparent, when viewed in conjunction with the following drawings, in which:

FIG. 1 is a side elevational view, in section, showing a containment device constructed according to the principles of the present invention;

FIG. 2 is a view similar to FIG. 1, with the containment device in its sealed configuration;

FIG. 3 is a side elevational view in section of a further embodiment of the present invention;

FIG. 4 is a view taken along the lines A—A of FIG. 3;

FIG. 5 is a view similar to FIG. 3, with the containment device in its sealed configuration.

DESCRIPTION OF THE PREFERRED EMBODIMENTS

Figure 6:
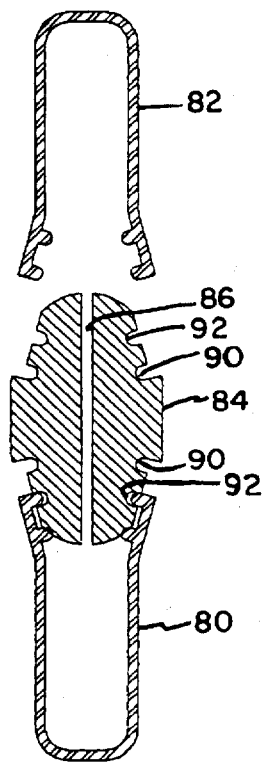
FIGS. 6, 7 and 8 represent side elevational views of yet a further embodiment of the present invention.

The present invention relates to a biological specimen containment tube 10 specifically for intra-vaginal placement of fertilized ovocytes.

The containment tube 10 is generally of cylindrical configuration having a first closed end 12 with a curved or somewhat hemispherical shape thereon. The containment tube 10 has a second open end 14 which is atmospherically sealable by a resilient plug 16 which is longitudinally movably disposed therein.

The second end 14 of the containment tube 10 has a slight outward directed flare with respect to the longitudinal axis of the containment tube 10, as shown by the angle "B", which angle is about 10 to 20 degrees, as represented in FIG. 1. The second end 14 of the tube 10 has an inner wall 18 which tapers to provide a decreasing inside diameter of the container in the direction away from the second end 14 of the tube 10. A first radially inwardly directed annular lip 20 is disposed on the surface of the inner wall 18, spaced apart from a second annular lip 22, the second annular lip 22, being arranged slightly more closely towards the middle of the of the containment tube 10.

The resilient plug 16 disposed in the second open end 14 of the containment tube 10 is shown at a first position in FIG. 1. The plug 16 has a narrow diameter, longitudinally directed central bore 24 therethrough. The plug 16 also has a slightly tapered outer annular surface 26, which increases in diameter from a rounded somewhat hemispherical inside surface 28 to its outer cap 30, shown by the angle "C" of about 10 to 20 degrees with respect to its longitudinal axis, as shown in FIG. 1.

The first inwardly directed annular lip 20 engages with a first annular groove 32 in the outer annular surface 26 of the plug 16, when the plug 16 is arranged in its first position, as shown in FIG. 1. This position permits the central bore 24 to remain open for the insertion of a pipette 36 into the chamber 38, which chamber is defined by the inner wall 40 of the containment tube 10

The plug 16 may be pressed inwardly into the containment tube 10, towards the first end 12, within the tapering walls 18 of the second end 14 of the tube 10, where the walls 18 of the tube and the second annular lip 32 tightly engage the first and second annular grooves 32 and 33 arranged in wall 26 of the plug 16. The resilient plug 16 is thereby squeezed radially inwardly, effectively blocking the longitudinally bore 24 extending therethrough, thus sealing whatever medium/culture has been inserted into the chamber 38 through that bore 24, as shown in FIG. 2. The rounded somewhat hemispherical shape on the inside surface 28 of the plug 16, permits any excess medium or gas in the chamber 38, to escape through the bore 24 of the plug 16, the rounded surface 28 eliminating any pooling or collection of air or gas within the chamber 38 as the plug is pushed tightly therein to engage all the grooves with annular lips.

A further embodiment of the containment tube 10 includes a walled cylindrically shaped chamber 50, having a rounded first end 52 and an open second end 54. The second end 54 has a curved, plastically resilient-walled cap 56 sealed thereon. The resilient-walled cap 56 has a central opening 58 through which a pipette, not shown here for clarity, may be inserted, for depositing of a biological specimen within the containment tube 10.

A resilient rubber-like cover 60 is engagably sealable over the resilient cap 56. The cover 60 has a hemispherical solid dome 62 with an annular lip 64 which extends off the edge of the hemispherical solid dome 62. An annular groove 66 is arranged on the inner wall 68 of the annular lip 64 to engage an annular lip 70 directed radially outwardly at the open end 54 of the containment tube 10. A planar surface 72 is arranged across the inside of the hemispherical dome 62. The cap 56 is shown in its open configuration, in the plan view of FIG. 4.

Placement of the cover 60 over the second end 54 of the containment tube 10 causes the planar surface 72 to frictionally engage the curved plastically resilient, walled cap 56, and displace it angularly inwardly, as shown by the arrows "A", in FIG. 3, towards the first end 52 of the containment tube 10. The angular displacement of the cap 56 brings its central opening 58 to a close, as shown in FIG. 5, and the annular lip 64 of the cover 60 sealing engages the outer side walls of the second end 54 of the containment tube 10, as shown in FIG. 5, thus absolutely minimizing any exposure time of any medium/culture to atmospheric gases or $CO_2$, providing a superior environment for cultivation and incubation of any ovocytes within the chamber 50.

Figure 7:
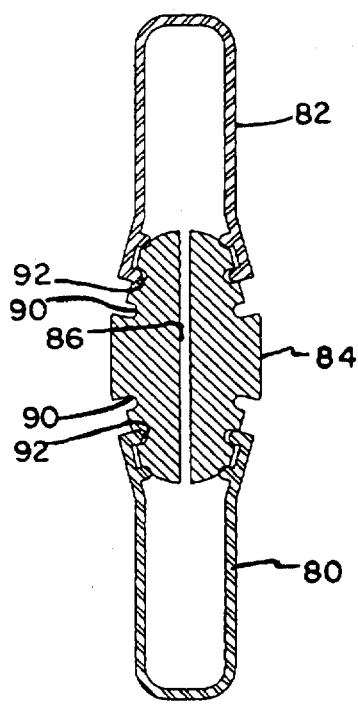
Figure 8:
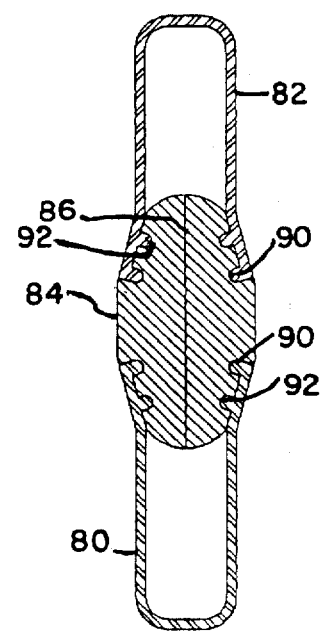

A further embodiment is shown in FIGS. 6, 7 and 8, wherein a pair of containment tubes 80 and 82 may be joined by a doable ended plug 84. Each containment to be 80 and 82 may be similar to the tube 10 shown in FIGS. 1 and 2. The plug 84 is essentially a mating of two plugs 16 joined each at their respective outer curved cap 30, having a common longitudinally aligned bore 86 therethrough.

The double ended plug 84 has a pair of annular grooves 90 and 92 at each respective side wall lips portions 94 and 96. The second groove 92 mates first with a first lip on each tube 80 or 82 is filled with a medium, both grooves 90 and 92 mate with their respective lips 94 and 96.

There may be a desire to transfer the contents of one tube 80 into another tube 82, without exposing any medium such as an embryo to the atmosphere, because such exposure would rapidly change the pH of any growth media and likely contaminate or kill any embryo therewith. One tube 80 would be filled and a double ended plug 84 inserted into its open end to seal it, locking both grooves 92 and 94 with both lips 94 and 96. The second tube 82 may be filled with a medium and the other end of the now inverted double ended plug 84 is pressed into the open end of the second tube 82. Transfer of an embryo from one tube 80 into the other tube 82 can be effected by backing out each end of the plug 84 to its outermost groove 92, thus unsqueezing the bore 86, permitting embryo/medium to be exchanged from one tube 80 to the other tube 82 without exposure to the atmosphere.

The invention further contemplates a pH indicator such as a litmus paper strip near the rounded inner end 28 of the plug 16 or 84.

Each tube 10, 80 or 82 may have an etched surface to permit marking thereon, as by etching or the like for identification purposes.

We claim:

1. A biological specimen container device comprising:

an elongated specimen container unit having a rounded closed first end an open second end to said container unit;

a cylindrically shaped containment wall disposed between said closed first end and said open second end; and a longitudinally pushable self-sealing cap having tapered outer walls arranged anchored to said second end of said container unit in a first open position and sealingly secured to said second end of said container unit in a second closed position thereat, said cap permitting deposit of material within said container unit while said cap is anchored in said first position.

said self-sealing cap and said second end of said container unit have a multiple lip and groove engagement arrangement therebetween, to permit anchoring and subsequent sealing of said container unit when said cap is moved from its first position to its second position in said open end of its container unit;

said cap comprising a plug having said tapered outer wall having a first and second spaced apart annular groove therearound said open second end of said container unit has a first and a second radially inwardly directed annular lip;

said first and second annular lips being spaced apart a distance which corresponds to the distance between said spaced apart annular grooves of said plug, said plug having an inner end which is spaced from said second annular groove a shorter distance than the distance of said spaced apart annular grooves on said plug, to permit said second groove to mate with said first lip without the inner end of said plug hitting said second lip, to permit safe securement of said plug to said container unit, and direct access to any specimen within said container unit.

2. The biological specimen container device as recited in claim 1, wherein said self-sealing cap has a squeezingly closable bore disposed longitudinally therethrough.

3. The biological specimen container device as recited in claim 1, wherein said tapered outer wall tapers at an angle of about 10 to 20 degrees with respect to the longitudinally axis of said container unit.

4. The biological specimen container device as recited in claim 1, wherein said plug has walls which taper at an angle of about 10 to 25 degrees with respect to the longitudinal axis of said plug.

5. The biological specimen container device as recited in claim 1, wherein said self-sealing cap is tapered on each end thereof, each end of said cap also having an arrangement of annular grooves thereon, for sealing said container unit on one end, and for sealing a second container unit on the other end, in longitudinal alignment with one another, each of said container units having corresponding annular lips thereon to mate with said grooves of said cap.

6. The biological specimen container as recited in claim 5, wherein said self-sealing cap has a mid-portion of wider diameter than said ends thereof, and a longitudinal bore extending through said cap, to permit fluid communication between said container units disposed on respective ends of said cap.

7. The biological specimen container as recited in claim 6, wherein a fluid content of one container may be transferred to said second container by loosening each end of said cap in its respective container, to permit said bore therein to become unsqueezed, and thereby patent, to permit such transfer without atmospheric contamination.

8. The biological specimen container as recited in claim 7, wherein said cap has a pH indicator on an inner end thereof.

9. A method of utilizing a biological specimen container, comprising the steps of arranging a cylindrically shaped containment unit, having a rounded closed first end and an open second end with walls therein defining a chamber;

arranging a taper in said walls of said open end of said containment unit;

arranging first and second spaced apart annular lips radially inwardly on said open end of said containment unit;

arranging first and second annular grooves on a plug being spaced apart a distance which corresponds to the distance between the spaced apart lips which are engagable with said annular lips on said containment unit to ensure a sealed relationship therebetween; and spacing said annular lips a distance farther apart than the distance apart of said second annular groove with respect to the inner end of the cap to permit said second annular groove to engage said first annular lip while securing said cap to said containment unit;

inserting said plug which is an anchorable flexibly sealable plug in a first position in said open second end of said containment unit wherein said second annular grove engages said first annular lip said plug having a patent bore extending longitudinally therethrough;

placing a pipette with biological specimens therein, through said bore in said plug, and into said containment unit;

releasing said biological specimens in said containment unit;

withdrawing said pipette from said patent bore of said plug; and pushing said plug from said first anchored position in said open end of said containment unit, to a second sealing position in said containment unit, wherein both the groves and lips engage and where said patent bore has been squeezed closed to effectively seal the biological specimen within said biological specimen container.

10. A biological specimen container device comprising;

an elongated specimen container unit having a rounded first closed end and an open second end;

a cylindrically shaped containment wall disposed between said first end and said open second end;

a flexible cap anchored to said open second end, said cap having an opening extending longitudinally therethrough for receipt of a specimen delivery tube therethrough said cap being distortable when moved from a first orientation to a second orientation, so that said opening therethrough is changed from a patent opening to a squeezed closed configuration said cap thus permitting deposit of material within said container unit while said cap is in its said first position; and wherein said flexible cap is of ovoid shape, and has a cover which mates thereover, so as to bias said cap into the second orientation effectively closing said opening in said cap and also proving a further seal to said container unit.

11. A biological specimen container as recited in claim 10, wherein said cover has an annular lip thereon, to sealingly engage said cylindrically shaped wall of said container unit.

12. A biological specimen container as recited in claim 11, wherein said cover has an annular groove on an inner wall surface of said annular lip, said annular groove being arranged to mate with a radially outwardly directed annular lip on said cylindrically shaped wall on said second end of said containment unit, to further seal any specimen in said container unit.

* * * * *